(12) United States Patent
Bekemeier et al.

(10) Patent No.: US 9,005,639 B2
(45) Date of Patent: *Apr. 14, 2015

(54) PROCESS FOR PREPARING SILICATE SHELL MICROCAPSULES

(75) Inventors: Thomas Bekemeier, Midland, MI (US); Lorry Deklippel, Piâton (BE); Tatiana Dimitrova, Braine L'Alleud (BE); Russell Elms, Midland, MI (US); Fabrizio Galeone, Buvrinnes (BE); Bertrand Lenoble, Silly (BE); Leon Marteaux, Auderghem (BE); Josef Roidl, Saulheim (DE); Martin Severance, Midland, MI (US); Stephane Ugazio, Soignies (BE); Brett Zimmerman, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 128 days.

This patent is subject to a terminal disclaimer.

(21) Appl. No.: 13/124,245

(22) PCT Filed: Oct. 15, 2009

(86) PCT No.: PCT/US2009/060824
§ 371 (c)(1),
(2), (4) Date: Aug. 8, 2011

(87) PCT Pub. No.: WO2010/045446
PCT Pub. Date: Apr. 22, 2010

(65) Prior Publication Data
US 2012/0021023 A1 Jan. 26, 2012

Related U.S. Application Data

(60) Provisional application No. 61/140,221, filed on Dec. 23, 2008, provisional application No. 61/176,226, filed on May 7, 2009, provisional application No. 61/181,728, filed on May 28, 2009.

(30) Foreign Application Priority Data

Oct. 15, 2008 (GB) .................................. 0818864.1

(51) Int. Cl.
| | | |
|---|---|---|
| A61K 8/02 | (2006.01) | |
| C11D 3/00 | (2006.01) | |
| A61K 8/11 | (2006.01) | |
| C11D 3/16 | (2006.01) | |
| C11D 3/37 | (2006.01) | |
| C11D 17/00 | (2006.01) | |

(52) U.S. Cl.
CPC ................ *C11D 3/0015* (2013.01); *A61K 8/11* (2013.01); *C11D 3/162* (2013.01); *C11D 3/3742* (2013.01); *C11D 17/0039* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,035,832 A | 7/1991 | Takamura et al. | |
| 5,506,201 A | 4/1996 | McDermott et al. | |
| 6,013,682 A | 1/2000 | Dalle et al. | |
| 6,251,313 B1 | 6/2001 | Deubzer et al. | |
| 6,303,149 B1 | 10/2001 | Magdassi et al. | |
| 6,737,444 B1 | 5/2004 | Liu | |
| 6,767,883 B2 | 7/2004 | Barbuzzi et al. | |
| 7,056,880 B2 | 6/2006 | Wang et al. | |
| 8,071,132 B2 * | 12/2011 | Adair et al. | 424/489 |
| 2004/0131570 A1 | 7/2004 | Suenaga et al. | |
| 2007/0088122 A1 | 4/2007 | Liles et al. | |
| 2008/0027172 A1 | 1/2008 | Gee et al. | |
| 2011/0158923 A1 | 6/2011 | Galeone et al. | |
| 2011/0165206 A1 | 7/2011 | Liu et al. | |
| 2011/0236498 A1 | 9/2011 | Marteaux et al. | |
| 2011/0311723 A1 | 12/2011 | Bekemeier et al. | |
| 2012/0021023 A1 | 1/2012 | Bekemeier et al. | |
| 2012/0101227 A1 | 4/2012 | Galeone et al. | |

FOREIGN PATENT DOCUMENTS

| | | |
|---|---|---|
| EP | 0590538 A1 | 4/1994 |
| EP | 0941761 A2 | 9/1999 |
| EP | 0958804 A2 | 11/1999 |
| WO | WO 02087522 A2 | 11/2002 |
| WO | WO 03066209 A1 | 8/2003 |
| WO | WO 2006063483 A1 | 6/2006 |
| WO | WO 2006072083 A1 | 7/2006 |
| WO | WO 2007049188 A1 | 5/2007 |
| WO | WO 2008002637 A2 | 1/2008 |
| WO | WO 2010045440 A1 | 4/2010 |
| WO | WO 2010045446 A2 | 4/2010 |

OTHER PUBLICATIONS

English language abstract for EP 0941761 extracted from the espacenet.com database on Oct. 11, 2011, 9 pages.
Dr. Alan Rawle, "Basic Principles of Particle Size Analysis", Malvern Instruments Limited, WR14 1XZ, UK, accessed on Oct. 11, 2011 through website: http://www.rci.rutgers.edu/~moghe/PSD%20Basics.pdf, 8 pages.
International Search Report for Application No. PCT/US2009/060817 dated Feb. 15, 2010, 3 pages.
International Search Report for Application No. PCT/US2009/060824 dated Jun. 16, 2010, 4 pages.
International Search Report for Application No. PCT/US2009/060836 dated Feb. 15, 2010 4 pages.

\* cited by examiner

*Primary Examiner* — Hasan Ahmed
(74) *Attorney, Agent, or Firm* — Howard & Howard Attorneys PLLC

(57) ABSTRACT

A process for preparing silicate shell microcapsules comprises adding a water reactive silicon compound to an oil in water emulsion, thereby condensing and polymerizing the water reactive silicon compound to form silicate shell microcapsules having a core comprising the oil phase of the said emulsion. The water reactive silicon compound comprises a tetraalkoxysilane and an alkoxysilane having an amino or quaternary ammonium substituted alkyl group.

17 Claims, No Drawings

PROCESS FOR PREPARING SILICATE SHELL MICROCAPSULES

RELATED APPLICATIONS

This application claims priority to and all the advantages of International Patent Application No. PCT/US2009/060824, filed on Oct. 15, 2009, which claims priority to Great Britain Patent Application No. GB0818864.1, filed on Oct. 15, 2008, U.S. Provisional Patent Application No. 61/140,221, filed on Dec. 23, 2008, U.S. Provisional Patent Application No. 61/176,226, filed on May 7, 2009, and U.S. Provisional Patent Application No. 61/181,728, filed on May 28, 2009.

This invention relates to silicate shell microcapsules having a core comprising an oil phase and a silicate shell, and to a process for preparing silicate shell microcapsules. The oil phase usually comprises an active material capable of imparting a desired property to a substrate to which the microcapsules are applied.

U.S. Pat. No. 6,303,149 describes a process for preparing sol-gel microcapsules loaded with functional molecules by emulsifying sol-gel precursors and the functional molecules in an aqueous solution, and mixing the emulsion with an acidic, neutral or basic aqueous solution to obtain a suspension of microcapsules.

EP-A-941761 describes a process for preparing microcapsules with an organopolysiloxane shell and a core material, in which the shell is formed in situ by hydrolysis and polycondensation of an organosilane and/or a condensation product thereof having at most 4 silicon atoms.

WO-A-03/066209 discloses a process for encapsulating a lipophilic cosmetic, chemical, biological or pharmaceutical active material composition, in which a water reactive silicon compound comprising tetraalkoxysilane is added to an aqueous emulsion of the active material composition having a positive zeta-potential, whereby the tetraalkoxysilane condenses and polymerises at the interface of the emulsified droplets of the lipophilic active material composition to form microcapsules having a core of the active material composition surrounded by a shell of silicon-based network polymer.

WO-A-2008/002637 discloses a process for preparing microcapsules by mixing an oil phase and an aqueous solution of a cationic surfactant to form an oil in water emulsion, and adding a water reactive silicon compound comprising tetraalkoxysilane to the emulsion so that the tetraalkoxysilane condenses and polymerises at the oil/water interface as described above. The amount of cationic surfactant is 0.1% to 0.3% by weight based on the oil phase and the shell thickness of the microcapsules is at least 18 nm.

The above prior patent applications relate mainly to encapsulation of sunscreens. Since sunscreens are effective in screening UV rays even when encapsulated, it is preferred that the rate of diffusion or leaching from the microcapsules is as low as possible when encapsulating sunscreen. Other active materials, however, may be ineffective if they are encapsulated with no diffusion or leaching from the microcapsules. The objective of encapsulation in this case is to achieve controlled diffusion or leaching from the microcapsules resulting in controlled release or prolonged release of the active material.

Examples of active materials for which controlled release is desired include additives for conditioning substrates like fabric, skin, hair and/or fibres, for example fabric softeners and hair conditioners. There is a demand for a conditioning composition that can be incorporated in a liquid cleaning product so that washing and conditioning can be carried out in a single process. However there is a risk that the conditioner is washed off the fabric or fibre by the cleaning product, particularly in a liquid laundry detergent. Lipophilic skin conditioners are prone to solubilisation in the surfactant—rich base of typical skin and hair cleaning compositions. The solubilised species are generally washed away and do not deposit on the skin or hair.

Examples of active materials for which prolonged release is desired include compositions which impart hydrophobicity, softness and flame retardant properties to textiles, particularly for the treatment of industrial textiles intended for uses such as mattress coverage, curtains, protective clothing, or tenting.

A process according to the invention for preparing silicate shell microcapsules comprises adding a water reactive silicon compound to an oil in water emulsion, thereby condensing and polymerizing the water reactive silicon compound to form silicate shell microcapsules having a core comprising the oil phase of the said emulsion, and is characterized in that the water reactive silicon compound comprises a tetraalkoxysilane and an alkoxysilane having an amino or quaternary ammonium substituted alkyl group.

The invention includes the use of an alkoxysilane having an amino or quaternary ammonium substituted alkyl group in the production of silicate shell microcapsules by adding a tetraalkoxysilane to an oil in water emulsion, whereby the alkoxysilane having an amino or quaternary ammonium substituted alkyl group modifies the silicate shell structure of the microcapsules produced.

We have found that the use of an alkoxysilane having an amino or quaternary ammonium substituted alkyl group in conjunction with a tetraalkoxysilane in the production of silicate shell microcapsules results in microcapsules which effectively encapsulate the oil phase but allow some diffusion or leaching from the microcapsules resulting in controlled release or prolonged release of the oil phase. This is surprising since amine groups and quaternary ammonium groups are condensation catalysts for hydrolysed alkoxysilanes. One might therefore expect condensation to happen throughout the aqueous phase of the emulsion, forming a gel, but we have found that the combination of tetraalkoxysilane and alkoxysilane having an amino or quaternary ammonium substituted alkyl group condenses on the interface of the emulsion droplets, resulting in microcapsules with good controlled release and prolonged release.

The alkoxy groups of the tetraalkoxysilane each have 1 to 4, preferably 1 or 2, carbon atoms. The tetraalkoxysilane can for example be tetraethoxysilane (TEOS), which can be used in monomeric form or as a liquid partial condensate.

The alkoxysilane having an amino or quaternary ammonium substituted alkyl group can contain one, two or three Si—OH groups or hydrolysable groups bonded to silicon and is preferably an aminoalkyltrialkoxysilane and/or a quaternised aminoalkyltrialkoxysilane. One preferred type of quaternised aminoalkyltrialkoxysilane has the formula $R'_3$—Si—Y—N(+)$R''_3$, wherein each group $R'$ is an alkoxy group having one or two carbon atoms, each group $R''$ is an alkyl group having 1 to 18 carbon atoms, and Y is a divalent hydrocarbon radical having 1 to 18 carbons. An example of such a quaternised aminoalkyltrialkoxysilane is dimethyl octadecyl trimethoxysilylpropyl ammonium chloride having the formula:

Examples of aminoalkyltrialkoxysilanes useful in the present invention include those having the formulae; $(CH_3O)_3$ $SiCH_2CH_2CH_2NH_2$, $(CH_3CH_2O)_3$ SiCH₂CH₂CH₂NH₂, or (CH₃CH₂O)₃SiCH₂CH₂CH₂NHCH₂CH₂NH₂

The water reactive silicon compound can for example comprise at least 10% by weight, for example 10 to 95%, tetraalkoxysilane, and up to 90% by weight, for example 5 to 90%, alkoxysilane having an amino or quaternary ammonium substituted alkyl group.

The tetraalkoxysilane and the alkoxysilane having an amino or quaternary ammonium substituted alkyl group are usually mixed before contacting the oil in water emulsion, so that a mixture of the tetraalkoxysilane and the alkoxysilane having an amino or quaternary ammonium substituted alkyl group is added to the emulsion. Alternatively the tetraalkoxysilane and the alkoxysilane having an amino or quaternary ammonium substituted alkyl group can be added separately but simultaneously to the oil in water emulsion, or can be added sequentially to the oil in water emulsion. If they are added sequentially, the tetraalkoxysilane is preferably added before the alkoxysilane having an amino or quaternary ammonium substituted alkyl group.

The oil phase can for example be a fabric or fibre conditioning agent, generally a lipophilic material which upon deposition on a fabric or fibres confers a benefit such as softening or shine or pleasant feel (touch). Conditioning agents within the scope of this patent are for example softening agents imparting softness to laundered fabrics and conditioning agents which facilitate the combing of hair. Without being bound to a theory, we believe that deposition of the conditioning agent on the fabric or fibres reduces of the sliding friction between fibers, whether these are the individual fibers and yarns used for the fabrication of textiles or biological fibers such as hair. This reduction in sliding friction is perceived as softness in fabrics and as a soft or silky feel in hair. Skin conditioning agents confer smooth feel to the skin and soothe the irritation caused by surfactants.

The conditioning agent can for example be an agent known as a fabric softener or an agent known as a hair conditioner. Polyorganosiloxanes are preferred conditioning agents within both these categories.

One preferred type of fabric softener is an amino-functional polyorganosiloxane. The amino-functional polyorganosiloxane can for example be a substantially linear amino-functional polydiorganosiloxane having at least one aminoalkyl group bonded to silicon. The organic groups of the polydiorganosiloxane can for example be alkyl and/or aryl groups and are usually methyl groups. One example of a preferred amino-functional polydiorganosiloxane has the formula:

$$Si(R^1)_3-O-(Si(CH_3)_2-O)_x-(Si(CH_3)R^*-O)_y-Si(R^1)_3,$$

where R* is an aminoalkyl group having 1 to 18 carbon atoms and 1 to 3 nitrogen atoms, each group $R^1$ is selected from alkoxy groups having 1 to 4 carbon atoms, hydrocarbon groups having 1 to 18 carbon atoms and or aminoalkyl groups having 1 to 30 carbon atoms and 1 to 5 nitrogen atoms, and x and y are integers between 1 and 100, y being less than 0.1 x. The aminoalkyl groups of the amino-functional polydiorganosiloxane are preferably of the formula:

$$R^2-(NH-A')_q-NH-A-$$

wherein A and A' are each independently a linear or branched alkylene group having 1 to 6 carbon atoms; q=0-4; $R^2$ is hydrogen or an alkyl or hydroxyalkyl group having 1 to 4 carbon atoms. Examples of preferred aminoalkyl groups include —(CH₂)₃NH₂, —(CH₂)₄NH₂, —(CH₂)₃NH(CH₂)₂NH₂, —CH₂CH(CH₃)CH₂NH(CH₂)₂NH₂, —(CH₂)₃NHCH₂CH₂NH(CH₂)₂NH₂, —CH₂CH(CH₃)CH₂NH(CH₂)₃NH₂, —(CH₂)₃NH(CH₂)₄NH₂ and —(CH₂)₃O(CH₂)₂NH₂.

Another preferred type of conditioning agent useful as a fabric softener is long-chain poly(organo)siloxane such as for example polydimethyl siloxane, which can be trimethyl or hydroxyl terminated. It is preferable to use DP (degree of polymerisation) of 800 and higher. Blends of different polysiloxanes can be used, for example of a polydimethyl siloxane with an amino-functional polyorganosiloxane.

Alternative polyorganosiloxanes useful as fabric softeners include silicone polyethers having a polydiorganosiloxane moiety, for example polydimethylsiloxane, and one or more hydrophilic polyalkylene oxide, for example polyoxyethylene chains. The hydrophilic polyalkylene oxide chains can be incorporated as side chains (pendant moieties) or as block copolymer moieties with the polysiloxane moiety.

The fabric softener can alternatively be an emulsifiable organic addition polymer, for example a dispersible polyolefin such as polyethylene or polypropylene modified by the inclusion of carboxyl groups.

Encapsulation of a fabric softener according to the invention can achieve controlled release of the fabric softener, for example when the softener is used in a liquid laundry composition. We have found that when fabrics are washed with a liquid laundry composition according to the invention containing an encapsulated fabric softening additive, improved softness of the fabrics is achieved compared to washing with the same liquid laundry composition containing the same amount of the same fabric softener which is not encapsulated, presumably due to improved retention of the softener on the fabric. We believe that encapsulation of the fabric softener protects it from solubilisation in the surfactant micelles of the wash, and that the fabric may act as a filter to retain the microcapsules, which subsequently break while rinsing and while spin drying to liberate the active fabric softener.

Preferred hair conditioners include amino-functional polyorganosiloxanes, for example substantially linear amino-functional polydiorganosiloxanes as described above. Unsubstituted polydiorganosiloxanes such as long chain polydimethylsiloxanes are also useful hair conditioners, for example the chain extended polydimethylsiloxanes produced as described in U.S. Pat. No. 6,013,682.

Preferred skin conditioners are lipophilic plant extracts (oils) and essential oils for example but not restricted to aloe vera, jojoba oil, chamomile oil; silicone based skin conditioners as dimethicone or dimethiconol, as well as synthetic oils as iso-dodecane, iso-hexadecane, paraffin, petrolatum, isononyl Isononanoate ester, octyldodecanol ester etc. These could be use alone or in combination.

Encapsulation of hair or skin conditioner according to the invention can give controlled release of the conditioner from a shampoo or shower gel. Lipophilic skin conditioners are prone to solubilisation in the surfactant—rich base of typical skin and hair cleaning compositions. The solubilised species are generally washed away and do not deposit on the skin or hair. Encapsulation can protect the conditioner from such solubilisation, and microcapsules produced according the invention can break when the shampoo is rubbed into the hair or skin.

The oil phase which is encapsulated can alternatively comprise a perfume. Controlled release of a perfume may be desired for example in a liquid laundry composition, so that fabrics after laundering are perfumed with a fresh smelling perfume such as lilial.

A fabric softener or a hair or skin conditioning agent may be encapsulated in a shell together with a perfume so as to provide an additive providing conditioning and perfuming benefits.

The oil phase can alternatively be a textile treatment composition intended to impart hydrophobicity, softness and/or flame retardant properties to textiles, particularly industrial textiles, on a long term basis.

The textile treatment composition can for example be a silicone composition comprising a single organopolysiloxane or a mixture of various organopolysiloxanes. The organopolysiloxanes may have any combination of $(R_3SiO_{0.5})$, $(R_2SiO)$, $(RSiO_{1.5})$, or $(SiO_2)$ units, commonly referred to as M, D, T, and Q units respectively, where R may be any monovalent organic group, usually methyl. The organopolysiloxanes may have cyclic, linear, or branched structures.

The silicone treatment composition may contain a siloxane resin containing at least one T or Q unit, as defined above. Typically, the siloxane resin contains at least 10 T or Q siloxy units. Thus, the siloxane resins useful in this invention could be any organopolysiloxane (or a mixture of organopolysiloxanes) of the formula $M_xD_yT_zQ_w$, where x, y, z, w represent the mole % of the corresponding units, with the proviso that x+y+z+w=100% and that z+w>10, alternatively z+w>30, or alternatively greater than 50. The siloxane resin may contain OH or hydrolysable to OH groups (as alkoxy for example) bonded to the Si atoms. Typically, 0.5 to 20% (mole) of the Si atoms should bear OH or hydrolysable groups.

In one embodiment, the siloxane resin is an MQ siloxane resin, for example a resin consisting essentially of $(CH_3)_3SiO_{1/2}$ units and $SiO_{4/2}$ units in the M:Q ratio of from 0.4:1 to 1.2:1, or a condensate of said MQ resin with other organosilicon compounds. For example, the MQ resin can be a siloxane resin copolymer consisting essentially of $(CH_3)_3SiO_{1/2}$ units and $SiO_2$ units in a molar ratio of approximately 0.75:1. A non-limiting example of such material is DC 5-7104 from Dow Corning Corp. (Midland, Mich.).

In another embodiment the siloxane resin is a DT resin, for example a resin consisting essentially of $(CH_3)_2SiO_{2/2}$ units and $(CH_3)SiO_{3/2}$ units in the D:T ratio of from 0.5:2 to 2:0.5. We have found that better durability results are obtained when 1 to 20% of the $CH_3$ groups are substituted with alkoxy radicals having one or two carbon atoms. Non-limiting examples of useful DT resins include DC 3037 and DC 3074 (Dow Corning Corp. Midland, Mich.). The siloxane resin can alternatively be a silsesquioxane resin consisting predominantly of T units.

The silicone treatment composition may contain a polydialkylsiloxane fluid having primarily D siloxy units of the formula $[R'_2SiO]$ where R' represents an alkyl group having 1 to 30 carbon atoms. The number of repeating D siloxy units (degree of polymerization) may vary but is such that the polydialkylsiloxane is a fluid at 25° C. In one embodiment, the polydialkylsiloxane fluid is selected from a trimethylsiloxy terminated polydimethylsiloxane fluid having a viscosity varying from 10 to 100,000 mm²/s at 25° C., alternatively from 60 to 60,000 mm²/s at 25° C., alternatively from 100 to 50,000 mm²/s at 25° C. Representative commercially available polydimethylsiloxane fluids include Dow Corning® fluids (Dow Corning Corporation, Midland Mich.). In another embodiment, the polydialkylsiloxane fluid is selected from a silanol terminated polydimethylsiloxane fluid having a viscosity varying from 10 to 100,000 mm²/s at 25° C., alternatively from 60 to 60,000 mm²/s at 25° C., alternatively from 100 to 50,000 mm²/s at 25° C.

In another embodiment, the silicone treatment composition contains a mixture of a siloxane resin as described above and a polydialkylsiloxane fluid as described above. The weight ratio of the polydialkylsiloxane fluid to the siloxane resin may vary, but typically is from 0.5/1 to 4/1, for example from 1/1 to 3/1.

The oil phase can alternatively or additionally comprise other compositions known for providing water or oil repellency to textiles, for example fluorocarbon based compounds such as various fluorocarbon oils, or fluorocarbon based polymers.

Other examples of oil phase materials which may be encapsulated are pharmaceuticals or sensitive chemical materials. Pharmaceuticals and related health products such as vitamins can be encapsulated in a silicon-based polymer shell which is broken down in the body after ingestion of the pharmaceutical. Biological (including biochemical) materials such as proteins, enzymes and cells can similarly be encapsulated. Radioactive material can be encapsulated for cancer treatment.

The oil phase is emulsified before being contacted with the water reactive silicon compound, so that the conditioning agent forms the disperse phase of an oil-in-water emulsion. The conditioning agent is emulsified in an aqueous medium preferably with the aid of a surfactant.

The surfactant is most preferably a cationic or amphoteric surfactant, which readily forms an emulsion of positive zeta-potential. We have found that a positive zeta-potential promotes condensation and polymerisation of the tetraalkoxysilane at the interface of the emulsified droplets of the conditioning agent, leading to more impervious microcapsules. Nonionic surfactants can be used; for example the cationic or amphoteric surfactant can be mixed with up to an equal weight of nonionic surfactant.

Examples of cationic surfactants include quaternary ammonium hydroxides such as cetyl trimethyl ammonium chloride, octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, fatty amines and fatty acid amides and their derivatives, basic pyridinium compounds, quaternary ammonium bases of benzimidazolines and polypropanolpolyethanol amines.

We have found that some alkoxysilanes having a quaternary ammonium substituted alkyl group can also act as a cationic surfactant. Part of the alkoxysilane having a quaternary ammonium substituted alkyl group required for shell formation can be used as a surfactant in forming the oil-in-water emulsion. Examples of suitable alkoxysilanes are 3-(alkoxysilyl)-propyl-N,N-dimethyl-alkylammonium chlorides, in which the alkoxy radical preferably has one or two carbon atoms and the alkyl radical is at least 12 CH2 groups long. The alkoxysilane having a quaternary ammonium substituted alkyl group can be dissolved in water, optionally with another surfactant such as a cationic or nonionic surfactant, to form the aqueous phase that is mixed with the oil phase to form an emulsion. The alkoxysilane having a quaternary ammonium substituted alkyl group can optionally be used in conjunction with a surfactant, for example a nonionic surfactant, which is dissolved in the oil phase.

Examples of suitable amphoteric surfactants include cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds.

The above surfactants may be used individually or in combination.

Examples of non-ionic surfactants include polyoxyalkylene alkyl ethers such as polyethylene glycol long chain (12-14C)alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol and alkylpolysaccharides, for example materials of the structure $R^i$—O—$(R^2O)_m$—$(G)_n$ wherein Ri represents a linear or branched alkyl group, a linear or branched alkenyl group or an alkylphenyl group, $R^2$ represent an alkylene group, G represents a reduced sugar, m denotes 0 or a positive integer and n represent a positive integer as described in U.S. Pat. No. 5,035,832.

The continuous aqueous phase of the emulsion can be a mixture of water with a water-miscible organic solvent such as an alcohol or lactam provided that the aqueous phase is not miscible with the conditioning agent.

The aqueous phase of the emulsion may contain a thickener, for example polyvinylpyrrolidone, polyvinyl alcohol, bentonite clay, a cellulose derivative, particularly a cellulose ether such as sodium carboxymethylcellulose, a lightly crosslinked acrylic polymer, modified starch, an alginate or xanthan gum, to inhibit settling of the microcapsules from the emulsion during formation or subsequently. The thickener is added to the emulsion before addition of the tetraalkoxysilane. Addition of polyvinylpyrrolidone to the emulsion before addition of the tetraalkoxysilane promotes formation of microcapsules more resistant to diffusion of the oil phase from the microcapsules for most particle sizes of the microcapsules.

The concentration of surfactant in the aqueous emulsion of conditioning agent can be between 0.01 and 10% by weight, but is preferably at least 0.02% and below 2%, most preferably 0.05 to 1.5% by weight of the emulsion, particularly 0.2-1.0%. In general the use of low levels of surfactant during emulsification of the conditioning agent and reaction with the alkoxysilane leads to microcapsules which are more resistant to diffusion or leaching of the conditioning agent from the microcapsules. Subsequent addition of surfactant to the suspension of microcapsules has less or no effect on diffusion or leaching of the conditioning agent from the microcapsules.

The weight ratio of oil phase to aqueous phase in the emulsion can generally be between 40:1 and 1:50, although the higher proportions of aqueous phase are economically disadvantageous particularly when forming an emulsion of microcapsules. Usually the weight ratio of oil phase to aqueous phase is between 2:1 and 1:10, and more preferably the oil phase (conditioning agent) forms from 10 or 20% up to 50% by weight of the emulsion.

We have found that, particularly when encapsulating a textile treatment composition to give prolonged release of the textile treatment, the concentration of cationic surfactant during the formation of the oil in water emulsion is preferably between 0.1% and 0.3% based on the weight of the oil phase.

Mixing and emulsion formation may occur using any known techniques in the emulsion art. Typically, the oil phase and an aqueous surfactant solution are combined using simple stirring techniques to form an emulsion. Particle size of the oil in water emulsion may then be reduced before addition of the tetraalkoxysilane by any emulsification device known in the art. Useful emulsification devices in this invention can be homogenizer, microfluidiser, sonolator, rotor-stator turbines, colloid mill, microfluidiser, blades, helix and combination thereof but is not limited to this list of emulsification devices. This further processing step reduces the particle size of the oil in water emulsion to values ranging from 0.1 to 500 µm, preferably 0.2 to 200 µm, with typical particle sizes ranging between 0.5 µm and 100 µm. Particle sizes lower than 30 µm are preferred, more preferably lower than 20 µm, more preferably lower than 16 µm, and preferably at least 1 µm. The emulsion particle size can for example be in the range 4 to 15 µm.

If the oil phase is highly viscous, a phase inversion process can be used in which the oil phase is mixed with surfactant and a small amount of water, for example 2.5 to 10% by weight based on the oil phase, forming a water-in-oil emulsion which inverts to an oil-in-water emulsion as it is sheared. Further water can then be added to dilute the emulsion to the required concentration.

The tetraalkoxysilane and the alkoxysilane having an amino or quaternary ammonium substituted alkyl group hydrolyse and condense to form a network polymer, that is a 3-dimensional network of silicon-based material, around the emulsified droplets of the conditioning agent. This network appears as a shell surrounding the droplets of conditioning agent.

The water reactive silicon compounds, that is the tetraalkoxysilane and the alkoxysilane having an amino or quaternary ammonium substituted alkyl group, can be added to the emulsion of conditioning agent as an undiluted liquid or as a solution in an organic solvent or in an emulsion form.

The weight ratio of the oil phase of the emulsion to water reactive silicon compound is preferably at least 0.5:1 and in many cases may be at least 1.5:1, for example 2:1 to 9:1. Smaller microcapsules, for example those formed from a microemulsion, generally have a lower ratio of oil phase to water reactive silicon compound.

The water reactive silicon compound and the emulsion are generally mixed under shear during addition and subsequently during condensation to form the silicon-based polymer shell on the surface of the emulsified droplets. Mixing can for example be by stirring, but it is preferred that the emulsion and the water reactive silicon compound are subjected to high shear, for example in a mixer of the rotor and stator type such as a Silverson (trade mark) mixer, either during addition of the water reactive silicon compound or after addition of the water reactive silicon compound and before formation of microcapsules is complete.

High shear mixing immediately after addition of the water reactive silicon compound is preferred. This leads to microcapsules of reduced particle size and appears to promote polymerisation of substantially all the water reactive silicon compound at the interface of the emulsion droplets.

The condensation reaction can be conducted at acidic, neutral or basic pH. The condensation reaction is generally carried out at ambient temperature and pressure, but can be carried out at increased temperature, for example up to 95° C., and increased or decreased pressure, for example under vacuum to strip the volatile alcohol produced during the condensation reaction.

Encapsulation of the oil phase can be achieved without any catalyst for the condensation reaction. However use of a catalyst may be preferred. Any catalyst known to promote the polymerization of alkoxysilanes may be present. The catalyst is preferably an oil soluble organic metal compound, for example an organic tin compound, particularly an organotin compound such as a diorganotin diester, for example dimethyl tin di(neodecanoate), dibutyl tin dilaurate or dibutyl tin diacetate, or alternatively a tin carboxylate such as stannous octoate, or an organic titanium compound such as tetrabutyl titanate. An organotin catalyst can for example be used at 0.05 to 2% by weight based on the water reactive silicon compound. An organotin catalyst has the advantage of effective catalysis at neutral pH. The catalyst is typically mixed with the oil phase components before it is emulsified, since this promotes condensation of the water reactive silicon compound at the surface of the emulsified oil phase droplets. A catalyst can alternatively be added to the emulsion before the addition of the water-reactive silicon compound, or simultaneously with the tetraalkoxysilane, or after the addition of the tetraalkoxysilane to harden and make more impervious the shell of silicon-based polymer which has been formed. The catalyst, when used, can be added undiluted, or as a solution in an organic solvent such as a hydrocarbon, alcohol or ketone, or as a mutiphasic system such as an emulsion or suspension.

The particle size of the microcapsules produced generally corresponds to the particle size of the starting emulsion. Microcapsules of particle diameter in the range 4 to 15 μm, for example 8 to 10 μm, may be particularly preferred. The diameter size of the microcapsules can be estimated with a microscope, for example by examining samples under a scanning electron microscope (SEM), or particle size measurements can be made by laser diffraction technique using a "Mastersizer 2000" from Malvern Instruments Ltd., UK, as described in the Examples below.

The shell thickness of the microcapsules depends on the weight ratio of conditioning agent to water reactive silicon compound and on the surface area of the emulsion droplets in the conditioning agent emulsion, which is inversely proportional to the droplet size for a given amount of conditioning agent. The shell thickness of the capsules is preferably in the range 2 to 100 nm, particularly between 5 and 50 nm. For capsules to be added to a liquid cleaning composition for controlled release, the preferred shell thickness may be between 5 and 20 nm, most preferably between 6 and 10 nm or between 10 and 15 nm. For capsules to be used in a textile treatment composition such as a flame retardant treatment to give a longer lasting effect, a greater shell thickness may be preferred, for example 25-40 nm. Microcapsules shell thicknesses are preferably determined by the physical relationships detailed in the Examples.

We have found that microcapsules of positive charge are preferred, particularly for textile treatment. The magnitude and the sign of the surface charge can be determined by measuring the zeta-potential (Z-potential) of the particles, for example using a Malvern Zetasiser instrument from Malvern Instruments Ltd. Instruments for measuring the Z-potential are also commercially available from Coulter Counter and others. The use of an alkoxysilane having an amino or quaternary ammonium substituted alkyl group according to the invention generally produces microcapsules of positive charge.

It may be preferred to recover the microcapsules from suspension. Recovery of the microcapsules can be achieved by any known liquid removal technique, for example by spray drying, spray chilling, filtering, oven drying or lyophilisation. The microcapsules can then be dispersed in the product in which they are to be used, for example in a liquid cleaning product such as a laundry composition or a shampoo, or a textile treatment composition which is to be applied to a fabric by padding, dipping, spraying or exhausting. Alternatively it may be preferred to add the suspension of microcapsules to the liquid cleaning product or textile treatment composition.

The encapsulated product can be post-treated with a water-reactive metal alkoxy or acyloxy compound. The metal compound should be gradually hydrolysed in water rather than immediately reacting with water; compounds of Group IVB, IVA or VA of the Periodic Table are suitable such as compounds of silicon, titanium, zirconium or vanadium. The water-reactive metal alkoxy or acyloxy compound can for example harden the shell of the microcapsules and/or make them more impermeable. The reactive metal alkoxy or acyloxy compound can for example be an alkoxysilane or acyloxysilane, particularly a trialkoxysilane such as methyl triethoxy silane or isobutyl triethoxy silane, or a silane having Si—H functionality such as tris(dimethylhydrogensilyloxy) n-octyl silane, or alternatively a titanium alkoxide (alkyl titanate).

The reactive metal alkoxy or acyloxy compound can have an organic functional group to promote adhesion to substrates, especially textile substrates, for example 3-methacryloxypropyl trimethoxy silane, 3-aminopropyl triethoxysilane, 3-aminopropyl trimethoxy silane, 3-glycidoxypropyl trimethoxy silane and 3-(2-aminoethylamino) propyl trimethoxy silane. The microcapsules can be post-treated with a reactive metal alkoxy or acyloxy compounds, e.g. an alkoxysilane to change their physical and/or chemical properties, for example by making the capsule surface more hydrophobic or more hydrophilic. For example, the microcapsule surface can be made more hydrophobic by reaction with a silane having a long chain alkyl group such as octyl triethoxy silane. As an alternative to chemical reaction the microcapsules can be coated with a material which alters their surface properties. The surface treatment can be carried out on the microcapsules in suspension or on the separated solid microcapsules.

The invention is illustrated by the following Examples.

EXAMPLE 1

25 g of an amino-substituted siloxane polymer useful as a fabric softener was emulsified as the oil phase in 70 g water using 0.4 g solution of cetriammonium chloride at 29% and 0.5 g glacial acetic acid. Resulting emulsion was characterised as having median particle size D05 of 10 μm.

1.5 g of a 50:50 by weight mixture of TEOS and 3-(trimethoxysilyl)-propyl-N, N-dimethyl-octadecylammonium chloride, (72 wt % in methanol, abbreviated N1) was added to the emulsion and the polymerisation was allowed to proceed for 12 hours. At the end of the polymerisation 2.4 g dispersant was added and the capsules were agitated for a further 2 hours.

EXAMPLES 2-8

These were prepared as Example 1, but varying the ratio between TEOS and quaternary ammoniumalkyl-trialkoxy silane N1. The amounts of TEOS and N1 used are shown in Table 1.

TABLE 1

| ingredients [g] | EXAMPLE | | | | | | | |
|---|---|---|---|---|---|---|---|---|
| | 1 | 2 | 3 | 4 | 5 | 6 | 7 | 8 |
| amino-siloxane | 25 | 25 | 25 | 25 | 25 | 25 | 25 | 25 |
| water | 70 | 70 | 70 | 70 | 70 | 70 | 70 | 70 |
| CTAC (29%) | 0.4 | 0.4 | 0.4 | 0.4 | 0.4 | 0.4 | 0.4 | 0.4 |
| acetic acid | 0.5 | 0.5 | 0.5 | 0.5 | 0.5 | 0.5 | 0.5 | 0.5 |
| TEOS | 0.75 | 1.485 | 1.425 | 1.35 | 1.2 | 0.6 | 0.375 | 0.3 |
| Quaternary alkoxysilane | 0.75 | 0.015 | 0.075 | 0.15 | 0.3 | 0.9 | 1.125 | 1.2 |
| Dispersant | 2.4 | 2.4 | 2.4 | 2.4 | 2.4 | 2.4 | 2.4 | 2.4 |

EXAMPLE 9

34 g hydroxy-terminated polydimethylsiloxane (PDMS) of DP=866 was emulsified in 63.9 g water using 0.4 g solution of cetriamonium chloride at 29%, 0.2 g of polyoxyethylene (3) lauryl ether and 0.2 g 2.5 M HCl. Resulting emulsion was characterised as having D05 of about 8 μm. A mixture of 1.3 g (50:50) TEOS and quaternary ammoniumalkyl-trialkoxy silane N1 was added, and the polymerisation was allowed to proceed for 12 hours to form a suspension of microcapsules.

EXAMPLES 10-13

Suspensions of microcapsules were prepared as described in Example 9 with ingredients described in Table 2.

TABLE 2

| ingredients [g] | Example | | | |
| --- | --- | --- | --- | --- |
| | 10 | 11 | 12 | 13 |
| Polymer | 34 | 34 | 34 | 34 |
| DP | 1000 | 866 | 1000 | 1000 |
| water | 63.9 | 63.9 | 63.9 | 63.9 |
| CTAC (29%) | 0.4 | 0.4 | 0.4 | 0.4 |
| 3-POE lauryl ether | 0.2 | 0.2 | 0.2 | 0.2 |
| HCl (2.5M) | 0.2 | 0.2 | 0.2 | 0.2 |
| TEOS | 0.65 | 0.65 | 1.04 | 1.04 |
| Quaternary alkoxysilane | 0.65 | 0.65 | 0.26 | 0.26 |
| D05 | 8 | 16 | 8.0 | 16 |

Particle size measurements here specified were made by laser diffraction technique using a "Mastersizer 2000" from Malvern Instruments Ltd., UK, and further information on the above particle sizes can e.g. be found in "Basic principles of particle size analytics", Dr. Alan Rawle, Malvern Instruments Limited, WR14 1XZ, UK and the "Manual of Malvern particle size analyser". Particular reference is made to the user manual number MNA 0096, Issue 1.0, November 1994. All particle sizes indicated in the present application were mean average particle size according to D(v, 0.5) and were measured with a Malvern Mastersizer; scattering pattern being analysed in the lines of the Mie theory.

Microcapsule shell thicknesses were determined by the following physical relationships:

Shell Thickness (nm)=$((D(v,0.5)/2)-(Dv0.5/2*(Payload/100)^{1/3}))*1000$

With:

D(v,0.5) expressed in microns.

Payload=Volume softening polymer*100/(Volume softening polymer+Volume shell).

Volume softening polymer=Weight softening polymer/Density softening polymer.

Volume shell=Weight shell/2.

The shell thicknesses of the microcapsules of Examples 1 to 13 are shown in Table 3.

TABLE 3

| EXAMPLE | SHELL THICKNESS |
| --- | --- |
| 1 | 18 |
| 2 | 12 |
| 3 | 12 |
| 4 | 13 |

TABLE 3-continued

| EXAMPLE | SHELL THICKNESS |
| --- | --- |
| 5 | 14 |
| 6 | 19 |
| 7 | 21 |
| 8 | 22 |
| 9 | 12 |
| 10 | 12 |
| 11 | 23 |
| 12 | 9 |
| 13 | 18 |

The suspension of microcapsules produced by each of Examples 9 to 13 was mixed with a commercial detergent at a ratio of 1% PDMS silicone active in the final blend. The blends obtained were observed using a Zeiss microscope equipped with long focus 20× objective (in this case AXIOPLAN from Zeiss) a sensitive live-image CCD camera (25 frames/second) connected to the frame grabber. The detergent capsules mixtures were loaded between standard microscope lamella and observed at regular time intervals.

In a comparative example, the emulsion of PDMS used in Examples 10, 12 and 13 was mixed with the same commercial detergent at a ratio of 1% PDMS silicone active in the final blend and observed using a microscope as described.

Very good dispersibility of the capsules was observed. The blends were then placed in a climatic chamber for 4 weeks at 40° C. At the end of the ageing process the blends were again observed using a microscope. No capsules or emulsion droplets were detected in the comparative example. The appearance of the detergents containing microcapsules produced in Examples 9 to 13 was similar to what was observed before ageing. Some traces of bulk silicone were detected on the walls of the containers of the detergents containing microcapsules produced in Examples 11 and 13. The microcapsules produced in Examples 9, 10 and 12, which have D05 below 15 μm are more stable than the larger microcapsules produced in Examples 11 and 13.

The microcapsules prepared in Examples 1, 2, 4 and 5 were mixed with a commercial liquid detergent at 3% amino-substituted siloxane polymer softener level. The modified detergents obtained were used in panel testing using the following protocol.

In a fabric pre-conditioning step to remove any silicone treatment made during manufacturing of fabrics, a load of 5 new pillow cases and 4 little terry towels (30×50 cm)=1.0 kg was washed 4 times in the following conditions:

Prewash 1: Miele W934—long program—water hardness: 0° F.–20 g Dash powder—Temperature: 95° C.—Spin rate: 600 rpm Blank 1: Miele W934—long program—water hardness: 0° F.—No detergent—Temperature: 95° C.—Spin rate: 600 rpm Prewash 2: same conditions that in prewash 1

Blank 2: same conditions that blank 1

In order to save some time, 3 loads could be preconditioned at the same time in the same washing machine. The total load is then 3.0 kg and the quantity of powder must be adjusted at 60 g.

In the fabric treatment step 2 or 3 treatments were made in parallel on 2 or 3 different washing machines at the same time. Each treatment comprised washing the load of 5 new pillow cases and 4 little terry towels with 20 g detergent. There was always one reference treatment washed with the commercial liquid detergent and 1 or 2 treatments with product to be tested. All fabrics from different treatments were line-dried at the same time at room temperature.

In the panel test, each panelist was presented two, three or four towels. One, two or three towels were treated with a product to be tested, and one was a reference washed with the commercial liquid detergent. One terry towel was used for 4 panellists and after was replaced by another one. Following questions were asked to 16 or 20 panellists.

"Which towel is the softer?"

"If the first fabric is the reference and quoted 5 on a scale of 1 to 10 how would you rate (the) other(s), considering 10 means very soft, smooth?"

Table 4 shows the results obtained with a panel of 16 testers. The 'Reference' is a commercial liquid detergent containing fabric softener sold under the Trade Mark 'Dash 2-in-1'.

TABLE 4

| Detergent | Example added | Average Score |
| --- | --- | --- |
| Reference | Nothing added | 5 |
| Commercial Detergent | Nothing added | 3.5 |
| Commercial Detergent | 2 | 3.9 |
| Commercial Detergent | 5 | 4.6 |
| Commercial Detergent | 1 | 4.8 |
| Commercial Detergent | 4 | 4.3 |

Towels treated with the detergents containing microcapsules prepared in Examples 1 and 5 were described as "substantially softer" than the towels washed by the detergent alone.

The microcapsules prepared in each of Examples 9 to 13 were mixed with a commercial liquid detergent at 1% PDMS softener level. The modified detergents obtained were used in panel testing using the protocol described above, As well as testing detergent containing microcapsules prepared in each of Examples 9 to 13 freshly added to the detergent, samples of the liquid detergent containing microcapsules prepared in Examples 9, 10 and 12 were aged for 4 weeks at 40° C. and then used to wash the towels. The results are shown in Table 5.

TABLE 5

| Detergent | Example added | Average Score fresh | Average score aged 4 w/40 C. |
| --- | --- | --- | --- |
| Reference | Nothing added | 5.0 | |
| Commercial Detergent | 9 | 5.9 | 5.2 |
| Commercial Detergent | 10 | 5.8 | 5.1 |
| Commercial Detergent | 11 | 5.7 | Not tested |
| Commercial Detergent | 12 | 5.9 | 6.1 |
| Commercial Detergent | 13 | 5.8 | Not tested |

The detergents containing microcapsules produced in each of Examples 9 to 13 gave better results when fresh than the Reference. Towels treated with the aged detergent comprising microcapsules according to the invention were positively perceived by the panellists, with the aged detergent comprising microcapsules produced in Example 12 giving better results than the Reference.

EXAMPLE 14

31 g of DC593 fluid (a blend of polydimethylsiloxane fluid (PDMS) having a viscosity of 100 mm$^2$/s at 25° C. and MQ resin at weight ratio of 67/33, available from Dow Corning Corporation of Midland, Mich., USA) were emulsified in 59 g water containing 0.4 g solution of cetriammonium chloride at 29% 0.2 g of lauryl alcohol ethoxylate (3 EO units) and 0.2 g 2.5 M HCl. The resulting emulsion was characterized as having D(v,0.5) in the range of 4 to 10 microns, depending on the level of the shear applied. Then 9.2 g of a 1:1 by weight mixture of TEOS and N1 was added with moderate agitation and allowed to polymerize for 18 hours. Capsules containing a core of resin—PDMS blend and a shell being composed of polymerized Si-network were obtained. Particle size measurements were made by laser diffraction technique using a "Mastersizer 2000" from Malvern Instruments Ltd., UK. All particle sizes indicated in the present application are mean average particle size according to D(v, 0.5)

EXAMPLES 15-28

Example 14 was repeated using various blends of silicone resin and PDMS and various ratios of TEOS and N1 as shown in Table 6. The total amount of polysiloxane (PDMS plus silicone resin if used) was the same in all these Examples, and the total amount of alkoxysilane (TEOS plus N1) was the same in all these Examples.

Comparative example C1 was carried out using TEOS without any alkoxysilane having an amino or quaternary ammonium substituted alkyl group. Comparative Examples C2 and C3 were non-encapsulated emulsions (i.e. neither TEOS nor N1 was added).

The compositions produced in Examples 14 to 28 and comparative examples C1 to C3 were each applied to Trevira (Trade Mark) CS polyester cotton flame retardant fabric and to cotton flame retardant fabric treated with Piruvatex (Trade Mark). Each fabric was treated using a standard padding machine. The formulation from Examples 14 to 28 and comparative examples C1 to C3 was diluted in water at 50 g/L and placed in the padding equipment. After the padding, the fabric was dried for 5 minutes at 120° C. and left at room temperature and controlled humidity for 24 hours before testing. The flame retardant properties were tested according the DIN 4102-B2. Table 6 below shows the results.

The treated fabrics were then tested for hydrophobicity, following a standard spray test described by the American Association of textile chemist and colourists. (AATCC 22). The hydrophobic properties were evaluated as described in AATCC 22. The following notation has been used to describe the softness:

"o"=some

"+"=some, but acceptable

"++"=good

"+++"=very good

The results are summarised in Table 6 in which all viscosity values are at 25° C.

TABLE 6

| Example | Resin/fluid | Ratio Resin/ 200 fl | Hydro-phobicity PE/COT | Softness PE/COT | Hydro-phobicity COTTON | Softness COTTON | D (v, 0.5) | Ratio TEOS N1 | Shell Thickness nm | Flame test |
|---|---|---|---|---|---|---|---|---|---|---|
| C1 | DC 593 | NA | 50 | O | 80 | o | 4.86 um | 100:0 | 33 | PASS |
| 14 | DC 593 | NA | 90 | + | 90 | + | 4.86 um | 1:1 | 51 | PASS |
| 15 | DC 593 | NA | 70 | ++ | 70 | ++ | 4.86 um | 1:3 | 60 | Not tested |
| C2 | DC 3037 DT resin/DC 200 PDMS fluid 100 mm²/s | 50/50 | 70 | + | 0 | + | 3 um | NA | 0 | PASS |
| 16 | DC 3037/DC 200 fluid 100 mm²/s | 50/50 | 50 | + | 70 | + | 3 um | 3:2 | 32 | PASS |
| 17 | DC 3037/DC 200 fluid 100 mm²/s | 50/50 | 70 | + | 70 | + | 0.44 u | 3:2 | 16 | PASS |
| 18 | DC 3074 DT resin/DC 200 fluid 100 mm²/s | 65/35 | 90 | O | 80 | o | 6.3 um | 3:2 | 68 | PASS |
| 19 | DC 3074/DC 200 fluid 100 mm²/s | 35/65 | 80 | O | 80 | o | 7.1 um | 3:2 | 73 | PASS |
| 20 | DC 3037/ | NA | 70 | ++ | 50 | + | 2/10 | 3:2 | 24 | PASS |
| 21 | DC 200 fluid 100mm²/s | NA | 80 | + | 0 | + | 4.3 um | 3:2 | 44 | PASS |
| 22 | Methoxy resin/DC 200 fluid 100 mm²/s | 35/65 | 70 | + | 0 | + | 4.3 um | 3:2 | 44 | PASS |
| 23 | DC 3074/DC 200 fluid 100 mm²/s | 65/35 | 80+ | | | | 2.7 um | 3:2 | 15 | PASS |
| 24 | PDMS Silanol terminated, 100 mm²/s | NA | 80 | ++ | 70 | ++ | 4.0 um | 3:2 | 43 | PASS |
| 25 | DC 3074/Silanol terminated PDMS14000 mm²/s | 65/35 | 80 | +++ | 70+ | +++ | 5.3 um | 3:2 | 57 | PASS |
| 26 | DC 3074/Silanol terminated PDMS 50000 mm²/s | 65/35 | 80 | +++ | 70+ | +++ | 5.6 um | 3:2 | 61 | PASS |
| 27 | PDMS Silanol terminated, 50000 mm²/s | NA | 90 | +++ | 90 | +++ | 3.0 um | 3:2 | 33 | PASS |
| 28 | PDMS Silanol terminated, 50000 mm²/s | NA | 90 | ++ | 90 | ++ | 10.0 um | 3:2 | 103 | PASS |
| C3 | PDMS Silanol terminated, 50000 mm²/s | NA | 0 | + | 0 | ++ | 3.6 um | NA | 0 | Not tested |

Different textiles were treated with the microcapsules produced in Examples 26 and 27, employing the method described in Example 14. In some cases, an anchorage enhancer has been added to the padding bath. The durability of the treatment was evaluated via the retention of the hydrophobicity after a multitude of washings. The latter were performed in a front loading European style washer, using a commercial detergent and a standard washing program for the particular type of textile. The results are summarized in Table 7.

TABLE 7

| Textile type | Composition of the padding bath | HYDROPHOBICITY | | |
|---|---|---|---|---|
| | | After preparation | One wash | Three washes |
| POLYESTER | Example 27 at 100 g/l | 100 | 70 | 70 |
| POLYESTER | Example 26 at 100 g/l | 80 | 70 | 70 |
| POLYESTER | Example 27 at 100 g/L + monoamino trialkoxysilane | 80 | 80 | 70 |
| POLYESTER | Example 26 at 100 g/L + monoamino trialkoxy silane | 80 | 70 | 70 |
| POLYESTER | Ex. 27 at 100 g/L + diamino trialkoxy silane | 80 | 70 | 70 |
| POLYESTER | Ex. 26 at 100 g/L + diamino trialkoxy silane | 80 | 80 | 80 |
| POLYESTER | Ex. 27 at 100 g/L + vinyl triacetoxysilane | 80 | 70 | 70 |
| POLYESTER | REFERENCE-untreated | 0 | 0 | 0 |
| COTTON | Example 27 at 100 g/L | 90 | 80 | 70 |
| COTTON | Example 26 at 100 g/L | 90 | 80 | 70 |
| COTTON | Example 27 at 100 g/L + monoamino trialkoxysilane | 80 | 50 | 50 |
| COTTON | Example 26 + monoamino trialkoxy silane | 70 | 0 | 0 |
| COTTON | Ex. 27 at 100 g/L + diamino trialkoxy silane | 80 | 50 | 50 |
| COTTON | Ex. 26 at 100 g/L + diamino trialkoxy silane | 70 | 0 | 0 |
| COTTON | Ex. 27 at 100 g/L + vinyl triacetoxysilane | 90 | 50 | 50 |
| COTTON | Example 27 at 100 g/L + melamine | 100 | 80 | 70 |
| COTTON | REFERENCE-untreated | 0 | 0 | 0 |

EXAMPLE 29

Example 27 was repeated using the same PDMS emulsion and the same total weight of alkoxysilane, but with the ratio of TEOS to N1 increased to 5.67:1 and with the alkoxysilanes being added sequentially. The TEOS was added first and the quaternary ammonium alkoxysilane N1 was added 4 hours later.

EXAMPLE 30

Example 29 was repeated using the same total weight of alkoxysilane, but with 73.5% of the TEOS being added initially and the remaining TEOS being added with N1 four hours later.

EXAMPLE 31

Example 30 was repeated, but with the remaining TEOS and the quaternary ammonium alkoxysilane N1 being added three hours later.

The surface charge of the capsules produced in Examples 14, 15, 27 and 29 to 31 and comparative example C1 was assessed via a standard zeta—potential measurement done on Malvern Zetasiser instrument equipped with a quartz cell. Results are described in Table 8

TABLE 8

| Ex | Core | TEOS:N1 ratio (addition method) | Shell (nm) | Zeta potential (mV) | Measurement conditions |
|---|---|---|---|---|---|
| C1 | DC 593 | 100:0 | 33 | −21 | pH 7, no salt |
| 14 | DC 593 | 1:1 (mixed TEOS and N1) | 51 | 60 | pH 7, no salt |
| 15 | DC 593 | 1:3 (mixed TEOS and N1) | 60 | 84 | pH 7, no salt |
| 27 | PDMS Silanol terminated | 3:2 (mixed TEOS and N1) | 33 | 44 | pH 7, no salt |
| 27 | PDMS Silanol terminated | 3:2 (mixed TEOS and N1) | 33 | 50 | pH 4, no salt |
| 27 | PDMS Silanol terminated | 3:2 (mixed TEOS and N1) | 33 | 35 | pH 4, 0.1M KCl |
| 29 | PDMS Silanol terminated | 5.67:1 (TEOS first, N1 4 h later) | 27 | 50 | pH 4, no salt |
| 29 | PDMS Silanol terminated | 5.67:1 (TEOS first, N1 4 h later) | 27 | 17 | pH 4, 0.1M KCl |
| 30 | PDMS Silanol terminated | 5.67:1 (73.5% of all TEOS first, the rest TEOS mixed with N1 4 h later) | 27 | 59 | pH 4, no salt |
| 30 | PDMS Silanol terminated | 5.67:1 (73.5% of all TEOS first, the rest TEOS mixed with N1 4 h later) | 27 | 17 | pH4, 0.1M KCl |
| 31 | PDMS Silanol terminated | 5.67:1 (73.5% of all TEOS first, the rest TEOS mixed with N1 3 h later) | 27 | 51 | pH 4, no salt |
| 31 | PDMS Silanol terminated | 5.67:1 (73.5% of all TEOS first, the rest TEOS mixed with N1 3 h later) | 27 | 24 | pH 4, 0.1M KCl |
| 31 | PDMS Silanol terminated | 5.67:1 (73.5% of all TEOS first, the rest TEOS mixed with N1 3 h later) | 27 | 39 | pH 7, no salt |

EXAMPLE 32

25 g of a hydroxy-terminated polydimethylsiloxane fluid with a viscosity of 50,000 mm$^2$/s was mixed to 1.0 g of deionised water, 0.20 g of Brij L4-LQ-(AP) non-ionic surfactant, and 0.16 grams of 3-(trimethoxysilylpropyl) octadecyltrimethyl ammonium chloride (72% in methanol) using a Hauschild Dental mixer. The resulting emulsion had a median size Dv05 of 3.8 um. This emulsion was diluted to 27.5% oil; the pH of the aqueous phase was brought to 4 and 8.04 g TEOS:N1 mix at ratio 60:40 were added under moderate agitation. The encapsulation was allowed to proceed to 24 h producing a stable dispersion of microcapsules.

The invention claimed is:

1. A process for preparing silicate shell microcapsules, the process comprising adding a water reactive silicon compound to an oil in water emulsion, thereby condensing and polymerizing the water reactive silicon compound in a reaction to form silicate shell microcapsules having a core comprising the oil phase of the emulsion, wherein the water reactive silicon compound comprises a tetraalkoxysilane and an alkoxysilane having an amino or quaternary ammonium substituted alkyl group.

2. The process according to claim 1 wherein the tetraalkoxysilane is tetraethoxysilane.

3. The process according to claim 1 wherein the alkoxysilane having an amino or quaternary ammonium substituted alkyl group is a quaternised aminoalkyltrialkoxysilane.

4. The process according to claim 3 wherein the quaternised aminoalkyltrialkoxysilane has the formula R'$_3$—Si—Y—N$^+$R"$_3$, wherein each group R' is an alkoxy group having one or two carbon atoms, each group R" is an alkyl group having 1 to 18 carbon atoms, and Y is a divalent hydrocarbon radical having 1 to 18 carbons.

5. The process according to claim 3 wherein the quaternised aminoalkyltrialkoxysilane has the formula $(CH_3O)_3SiCH_2CH_2CH_2N^+(CH_3)_2(CH_2)_{17}CH_3Cl—$.

6. The process according to claim 1 wherein a mixture of the tetraalkoxysilane and the alkoxysilane having an amino or quaternary ammonium substituted alkyl group is added to the oil in water emulsion.

7. The process according to claim 1 wherein the tetraalkoxysilane and the alkoxysilane having an amino or quaternary ammonium substituted alkyl group are added sequentially to the oil in water emulsion.

8. The process according to claim 1 wherein the aqueous phase of the oil in water emulsion contains a cationic surfactant.

9. The process according to claim 1 wherein the oil phase comprises 10 to 50% by weight of the oil in water emulsion.

10. The process according to claim 1 wherein the median particle size of the oil phase of the oil in water emulsion is 2 to 30 μm.

11. The process according to claim 1 wherein the oil phase of the oil in water emulsion, which becomes encapsulated in the silicate shell microcapsules, comprises a fabric, skin, hair or fibre conditioning agent.

12. The process according to claim 11 wherein the oil phase of the oil in water emulsion, which becomes encapsulated in the silicate shell microcapsules, comprises a fabric conditioning agent, wherein the fabric conditioning agent further comprises a silicone textile treatment composition.

13. A process of using an alkoxysilane having an amino or quaternary ammonium substituted alkyl group for producing silicate shell microcapsules, the process comprising adding a tetraalkoxysilane and the alkoxysilane having an amino or quaternary ammonium substituted alkyl group to an oil in water emulsion; and reacting the tetraalkoxysilane and the alkoxysilane having an amino or quaternary ammonium substituted alkyl group to form the silicate shell microcapsules, whereby the alkoxysilane having an amino or quaternary ammonium substituted alkyl group modifies a silicate shell structure of the microcapsules produced.

14. The process according to claim 13, whereby the alkoxysilane having an amino or quaternary ammonium substituted alkyl group confers to the silicate shell structure of the microcapsules a positive surface charge as measured by zeta-potential.

15. The process according to claim 2 wherein the alkoxysilane having an amino or quaternary ammonium substituted alkyl group is a quaternised aminoalkyltrialkoxysilane.

16. The process according to claim 15 wherein the quaternised aminoalkyltrialkoxysilane has the formula R'$_3$—Si—Y—N$^+$R"$_3$, wherein each group R' is an alkoxy group having one or two carbon atoms, each group R" is an alkyl group having 1 to 18 carbon atoms, and Y is a divalent hydrocarbon radical having 1 to 18 carbons.

17. The process according to claim 15 wherein the quaternised aminoalkyltrialkoxysilane has the formula $(CH_3O)_3SiCH_2CH_2CH_2N^+(CH_3)_2(CH_2)_{17}CH_3Cl^-$.

* * * * *